United States Patent [19] [11] 4,050,307
McMullen et al. [45] Sept. 27, 1977

[54] DIAL HUMIDITY INDICATOR FOR CONTAINERS

[75] Inventors: Willard C. McMullen, Little Falls, N.J.; Samuel Gee, Sr., deceased, late of Denville, N.J.; by Patricia E. Whitney, legal representative, Frankfort, Ill.; by Joan E. Bennett, legal representative, Chula Vista, Calif.

[73] Assignee: The United States of America as represented by the Secretary of the Army, Washington, D.C.

[21] Appl. No.: 610,026

[22] Filed: Sept. 3, 1975

[51] Int. Cl.² .................................... G01N 19/10
[52] U.S. Cl. .................................... 73/337; 73/431
[58] Field of Search ............ 73/73, 335, 337, 337.5, 73/334, 431, 430; 200/61.06; 116/124 S

[56] References Cited

U.S. PATENT DOCUMENTS

| | | | |
|---|---|---|---|
| 2,611,481 | 9/1952 | Sargeant et al. | 73/431 X |
| 2,887,544 | 5/1959 | Gustausson | 73/337 X |
| 2,934,954 | 5/1960 | Phillips | 73/335 |
| 2,942,469 | 6/1960 | LeRoy | 73/334 |
| 3,142,287 | 7/1964 | Jones | 73/73 X |
| 3,243,536 | 3/1966 | Hansen | 200/61.06 |
| 3,345,872 | 10/1967 | Meginnis | 73/334 |
| 3,625,390 | 12/1971 | Meginnis | 73/334 X |
| 3,763,338 | 10/1973 | Tozer | 73/337.5 X |

*Primary Examiner*—S. Clement Swisher
*Assistant Examiner*—John S. Appleman
*Attorney, Agent, or Firm*—Nathan Edelberg; A. Victor Erkkila; Max Yarmovsky

[57] ABSTRACT

A dial humidity indicator for containers utilizes a shock mounted sensing mechanism having an expansible tensioned sorption element, and a pressure-tight, window-type plug to position the indicator in the container wall. The present device, when mounted in the wall of an hermetically sealed shipping container, provides rapid, accurate and continuous readings of relative humidity at the extremes of relative humidity and temperature under severe shock and vibration conditions.

5 Claims, 4 Drawing Figures

DIAL HUMIDITY INDICATOR FOR CONTAINERS

GOVERNMENTAL INTEREST

The invention described herein may be manufactured, used and licensed by or for the Government for governmental purposes without the payment to us of any royalty thereon.

BACKGROUND OF THE INVENTION

Many materials, particularly military supplies, are packaged under controlled relative humidity (R.H.) conditions in order to protect them from deterioration. One of the prior art methods for monitoring R.H. in containers was based on viewing a chemically impregnated card through an air-tight window held in a button type plug package which was sealed in an orifice in the container wall. The chemically impregnated card had treated marked spots thereon which responded by changing color when the relative humidity was within a specific range. The button type package humidity card indicator has been described in U.S. Pat. No. 2,716,338. The aforedescribed prior art device had problems because it was often difficult for an observer to read the cards and distinguish with assurance whether the color was blue, blue-pink, or pink. Since the color reading was subjective from person to person, it was very difficult to get an accurate reading. In addition, people who are color-blind would have additional problems in making a proper determination of the exact reading. Another problem with the prior art chemical card type indicator was that, after extended usage, the chemicals tended to leach out of the cards thereby making the readings indistinguishable. Another problem with the go-no go type of card indicator was that it was not possible to determine how far the atmosphere in the container was above or below a determined critical level of R.H. Such information is desirable during humidity control conditioning of the container after loading, and also when the container is exposed to temperature changes. A further problem with the prior art card device was that it was not possible to monitor humidity in a container with reasonable precision when using disc indicators. Experience has shown that R.H. readings taken with color change indicators may be off the actual value by as much as 20%.

SUMMARY OF THE INVENTION

The present invention relates to a dial humidity indicator whose primary application is for monitoring the relative humidity condition in containers, and particularly, containers for aircraft engines, missiles, missile sections, munitions and other complex and costly hardware. The present invention comprises a combination of a dial humidity indicator, having an expansible tensioned sorption element, synergistically combined with a pressure-tight-window-type plug that can be readily mounted in an orifice located in the wall of the container to be monitored. The present device when mounted in an hermetically sealed container is capable of accurately functioning at extremes of R.H. and temperature despite the shock and vibration forces normally experienced in transportation. The present invention, because of the use of a nylon sorption element, can measure relative humidity without being appreciably affected by temperature variations. The present invention utilizes a mounting arrangement which is water vapor proof and therefore is not affected by the ambient level of water vapor outside of the container being monitored. In addition, the present device is self-powered and therefore requires no manipulation of the sensing mechanism by the observer to obtain a relative humidity reading. Because the present invention is relatively small in size, occupying less than 5 cubic inches in volume, it can be used advantageously in containers which have limited space. The present device utilizes a stable and durable nylon type expansible tensioned element; thus its readings and calibration tend to maintain their accuracy better than the aforedescribed prior art combination.

An object of the present invention is to provide a dial humidity indicator that is easy to read.

Another object of the present invention is to provide a dial humidity indicator that maintains its accuracy over a prolonged period of time.

Another object of the present invention is to provide a dial humidity indicator for an hermetically sealed container that responds to changes in relative humidity within several minutes.

Another object of the present invention is to provide a dial humidity indicator for a sealed container that can readily be connected thereto by an hermetic seal.

Another object of the present invention is to provide a dial humidity indicator for an hermetically sealed container that can be readily transported because it is shock and vibration resistant.

Another object of the present invention is to provide a dial humidity indicator, for use in sealed containers, which gives readings substantially independent of temperatures in the range of $-65°$ to $+160°$ F.

Another object of the present invention is to provide a dial humidity indicator, for use in sealed containers, which is compact in size.

Another object of the present invention is to provide a dial humidity indicator, for use in a sealed container, wherein the sensing element is protected from damage from the contents carried by the container.

A further object of the present invention is to provide a dial humidity indicator, for containers, which is of moderate cost.

For a better understanding of the present invention, together with other and further objects thereof, reference is made to the following descriptions taken in connection with the accompanying drawings.

BRIEF DESCRIPTION OF THE DRAWINGS

Throughout the following description like reference numerals are used to denote like parts of the drawings.

DESCRIPTION OF THE PREFERRED EMBODIMENTS

Figure 2:
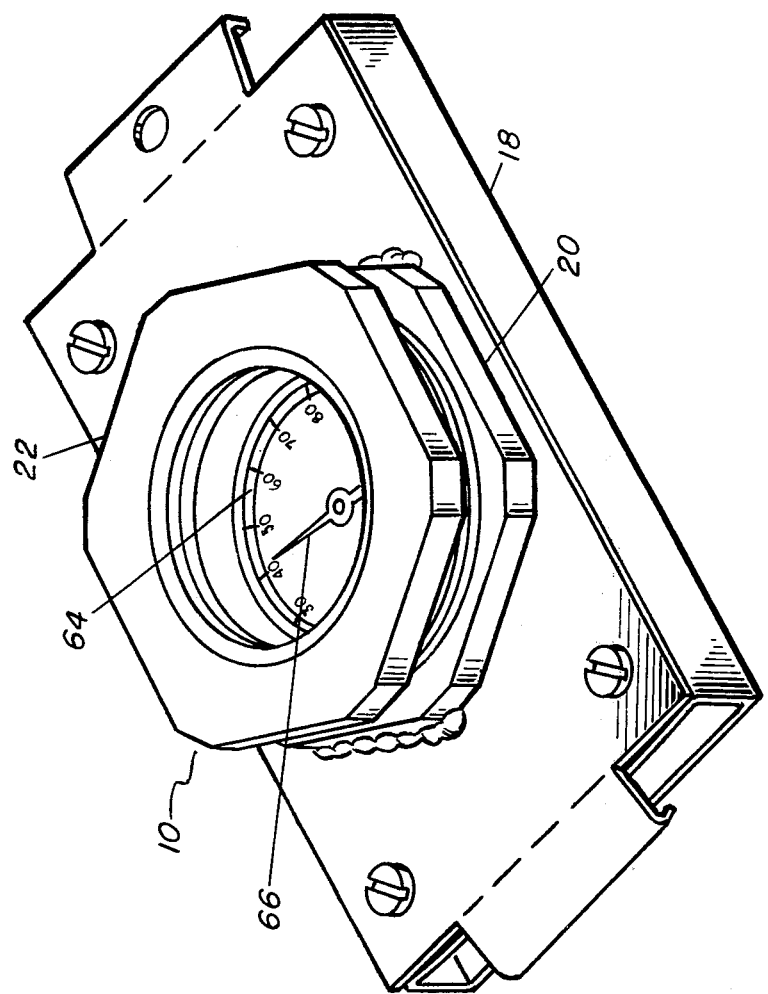
FIG. 2 is an isometric top view of the humidity dial indicator with its protective enclosure.
Figure 1:
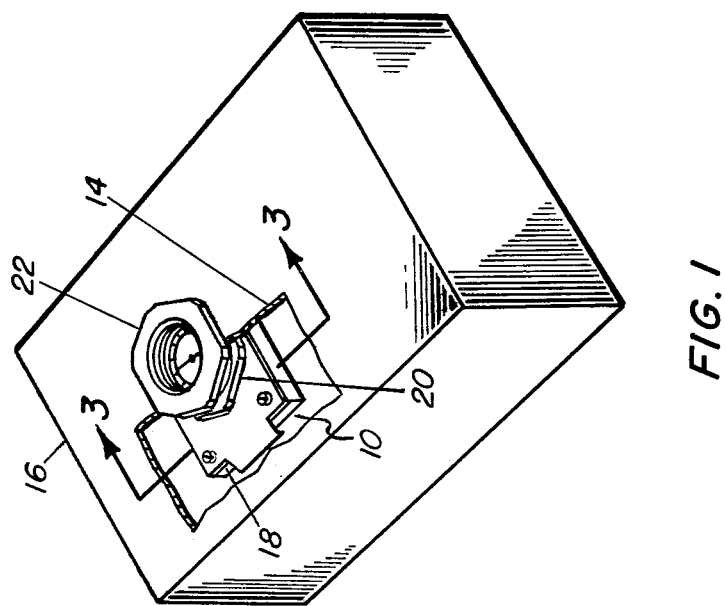
FIG. 1 is an isometric fragmentary view of the humidity dial indicator device positioned in an hermetically sealed container.
Figure 3:
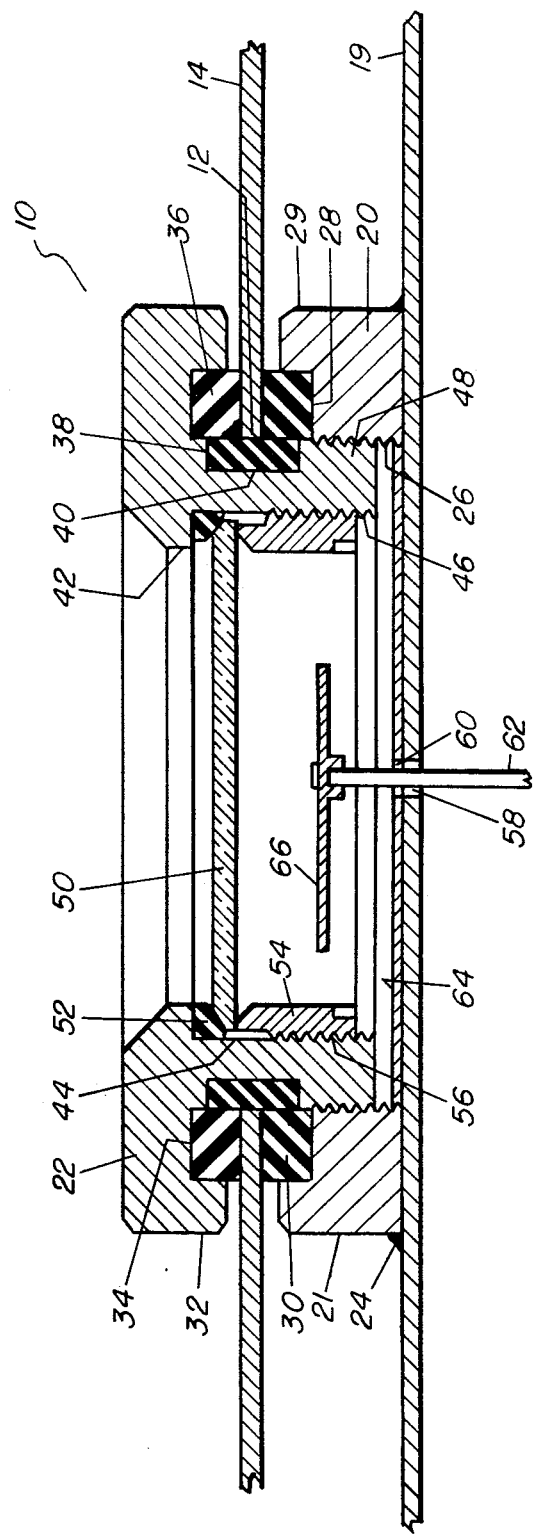
FIG. 3 is a partial cross-sectional view taken along line 3—3 of FIG. 1.

Referring now to FIGS. 1, 2 and 3, indicator plug assembly 10 is fixedly positioned in a bore 12 of the wall 14 of an hermetically sealed container 16. A perforated indicator body housing 18, which protects the indicator sensing element, described in further detail herein, is positioned inside of container 16 by a tubularly shaped hexagonal base member 20 and a hexagonally shaped viewing nut member 22. Hexagonal base member 20 bottom end 21 is fixedly attached to mounting plate 19 by weld 24; plate 19 is in turn affixed to body housing 18. Base member 20 has an internally threaded bore 26 therein and a shallow base counterbore 28, in its top end 29. Counterbore 28 holds a first rubber washer 30 partially therein. Nut member 22 has a shoulder 32 thereon which contains an annular shoulder groove 34 therein which is concentric with base member counterbore 28. A second rubber washer 36 is partially positioned within annular shoulder groove 34. A third annular rubber washer 38 is located within annular shaft groove 40. The aforementioned three rubber washers 30, 36 and 38 respectively perform the dual function of providing a compliant shock mounting and air-tight seal for the indicator plug assembly 10 when it is positioned in container wall 14. Nut member 22 has an axially aligned sight bore 42 therein which communicates with counterbore 44 which has a partially internally threaded bore 46 therein. Nut member 22 has a partially externally threaded shaft end 48. Threaded shaft end 48 threadedly engages base threaded bore 26, and forcibly holds container wall 14 intermediate first and second washers 30 and 36 respectively. A disc shaped sight glass 50 is forcibly held intermediate "O" ring 52 and ring member 54 when the ring member's externally threaded end 56 threadedly engages threaded bore 46. Mounting plate 19 has a pointer shaft bore 58 therein which is in axial alignment with a dial face axial bore 60. Shaft bore 58 and axial bore 60 permit pointer shaft 62 to freely pass therethrough. A disc shaped dial plate 64 having a circularly marked scale thereon is fixedly positioned on mounting plate 19 beneath sight glass 50 so that an observer looking into sight bore 42 can observe the relative position of pointer 66 against the scale of dial plate 64.

Figure 4:
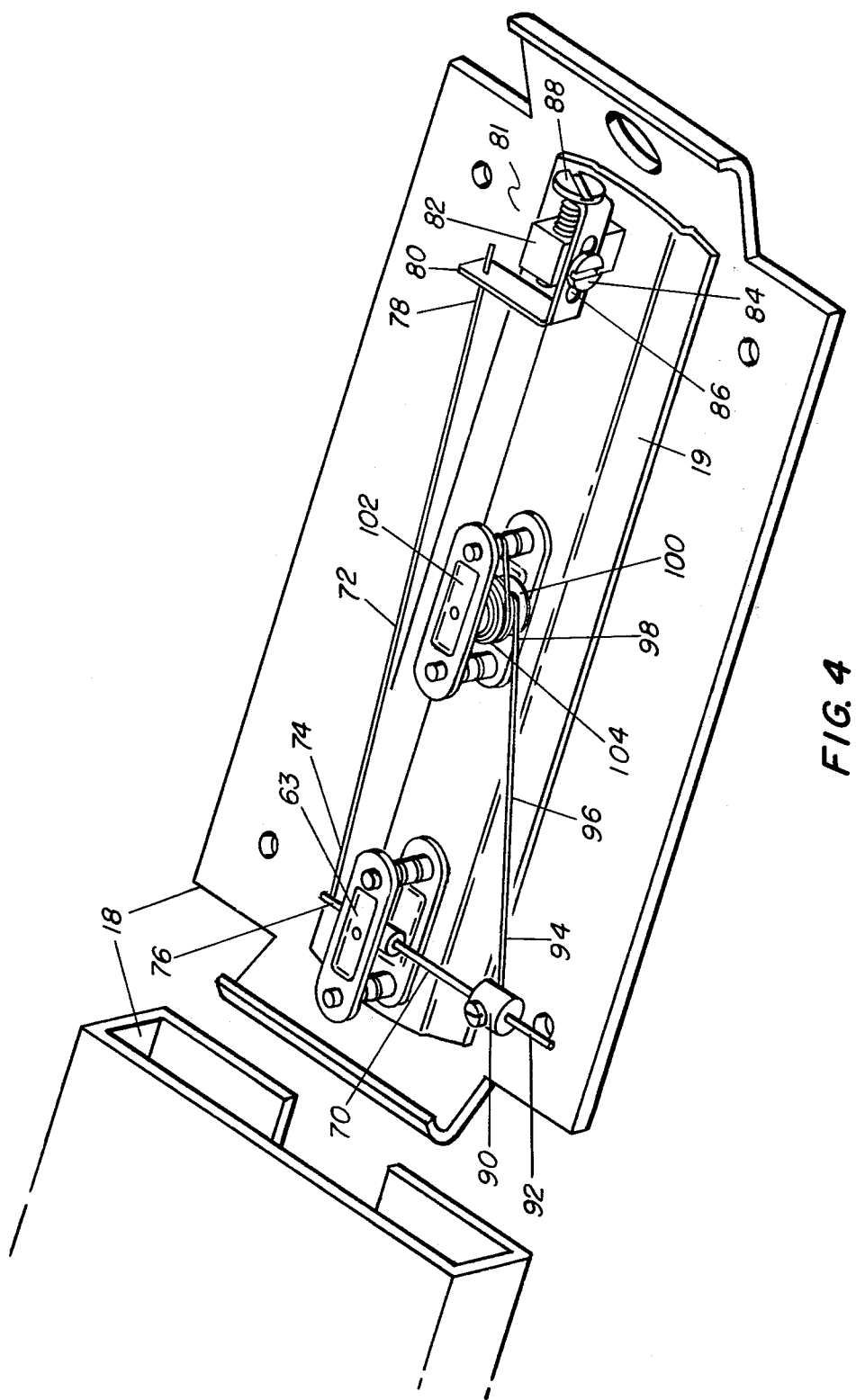
FIG. 4 is an isometric back view of the humidity dial indicator sensing mechanism.

Referring now to FIG. 4, the other side of mounting plate 19 supports a first pivot assembly 68 which in turn rotatably supports pivot arm 70. A moisture sensitive expansible sorption element 72, such as nylon cord, has one end 74 attached to a first end 76 of pivot arm 70 and the other cord end 78 is attached to a zero adjustment "U" shaped member 80 of zero adjustment assembly 81 which is affixed to mounting plate 19. "U" shaped member 80 is slidably held to zero adjustment post 82 by a screw 84 whose shank slidably passes through slot 86. When adjustment screw 88 is made to bear against post 82 the movement causes the "U" shaped bracket 80 and the linkages attached thereto to move. A slide member 90 is adjustably positioned on the other end 92 of pivot arm 70 and holds a first end 94 of a second expansible cord element 96, which may be made of such material as nylon. The other cord end 98 is wrapped around a pulley 100 which is attached to the back end of pointer shaft 62 which is in turn rotatably supported by a second pivot assembly 102. A torsionally biased coil spring 104 is positioned intermediate the pulley 100 and the pivot assembly 102, in such manner as to cause the pulley 100 to rotate and take up the slack in cords 72 and 96.

In operation, after the base member 20 with its attached mounting plate 19 and protective housing 18 are located in a container 16 opposite the container wall bore 12, the hexagonally shaped viewing nut member 22 is screwed to the hexagonal base member 20 and tightened down to provide an air-tight, ruggedized seal. The cords 72 and 96 expand and contract in response to changes in the R.H. of the air in the sealed container. Expansion or contraction of first cord 72 is magnified nearly two times by the pivot arm 70. Adjustment for ranging is provided by moving the slide 90 to the left of FIG. 4 to increase range and to the right to decrease range. As previously stated, the lower end 98 of second cord 96 is wrapped around pulley 100 which is in turn mounted on the pointer shaft 62. When the cords 72 and 96 shorten due to reduced humidity within the container, the pulley 100 is rotated and the attached pointer 66 moves toward the zero % R.H. on the scale 64. When the cords 72 and 96 lengthen due to increased humidity within the container, the coil spring 104 drives the pulley in the other direction so that the pointer 66 moves toward 100% R.H. on the scale 64. A zero setting is obtained by advancing or retarding adjustment screw 88. This adjustment moves the first cord end 87 closer to or further away from the pivot arm 70 and results in moving the pointer 66 closer to or away from the 0% R.H. mark on scale 64.

The foregoing disclosure and drawings are merely illustrative of the principles of this invention and are not to be interpreted in a limiting sense. We wish it to be understood that we do not desire to be limited to the exact details of construction shown and described for obvious modifications will occur to a person skilled in the art.

Having thus fully described the invention, what is claimed as new, useful and non-obvious and desired to be secured by Letters Patent of the United States is:

1. A dial humidity indicator for attachment to a container which comprises:
    dial indicating and sensing means adapted to be disposed within said container for measuring the percentage of relative humidity therein;
    sealed viewing means for observing said indicating means from outside said container; and means, for holding said sensing means and said viewing means to said container so that they are shock isolated therefrom and hermetically sealed thereto.

2. A dial humidity indicator as recited in claim 1 wherein said dial indicating and sensing means comprises:
    a perforated body housing for protecting said sensing means;
    a mounting plate fixedly attached to said perforated body housing, said mounting plate having a pointer shaft bore therein;
    a disc shaped dial plate having a circularly marked scale thereon and an axial bore therein, said dial plate being affixed to one side of said mounting plate so that said axial bore is axially aligned with said pointer shaft bore;
    a tubularly shaped base member having a threaded bore therein and a shallow base member counterbore in the top end of said base member, said base member being fixedly attached to said mounting plate so that said threaded bore is concentric with said shaft bore;
    a first pivot assembly fixedly positioned to the other side of said mounting plate;
    a pivot arm rotatably supported by said pivot assembly;
    a first moisture sensitive expansible sorption cord element having one end fixedly attached to a first end of said pivot arm;

a zero adjustment assembly fixedly attached to said mounting plate movably holds the other end of said expansible sorption cord;

a slide member adjustably positioned on the other end of said pivot arm;

a second moisture sensitive expansible sorption cord element having one end fixedly attached to said slide member;

a second pivot assembly fixedly positioned to the other side of said mounting plate;

a torsionally biased pulley rotatably supported by said second pivot assembly, said pulley being connected to the other end of said second expansible sorption cord element;

a pointer shaft axially connected on one end to said pulley and extending through said mounting plate shaft bore and said dial plate axial bore; and a pointer transversely positioned on the other end of said pointer shaft, wherein, when said first and second expansible cord elements shorten due to reduced humidity within said container, said pulley and pointer shaft are rotated so that said pointer moves toward a zero % relative humidity marking on said dial plate, and when said first and second expansible sorption cord elements lengthen due to an increase in humidity within said container, said biased pulley rotates said pointer in an opposite direction to cause said pointer to move toward a 100% relative humidity marking on said dial plate.

3. A dial humidity indicator as recited in claim 2 wherein said first moisture sensitive expansible sorption cord is made of nylon.

4. A dial humidity indicator as recited in claim 2 wherein said second moisture sensitive expansible sorption cord is made of nylon.

5. A dial humidity indicator as recited in claim 2 wherein said sealed viewing means comprises:

a nut member having a shoulder thereon which contains an annular shoulder groove therein, a shaft end, a partially internally threaded counterbore, a sight bore of slightly smaller size than said internally threaded counterbore which communicates with said internally threaded counterbore, and an annular shaft groove positioned near said shoulder groove and intermediate said shoulder and said shaft end;

an "O" ring positioned in said partially threaded counterbore;

a disc shaped sight glass positioned in said partially threaded counterbore, said sight glass having one side in contact with said "O" ring;

a threaded ring member threadedly engaging, said internally threaded counterbore and forcibly holding said sight glass against said "O" ring to provide an hermetic seal between said sight glass and said nut member; and wherein said means for holding comprise external thread means formed on said shaft end of the nut member for threaded engagement with said threaded bore of the base member through a bore formed in a wall of said container, a first annular rubber washer positioned in said counterbore of the base member; and second and third annular rubber washers respectively positioned in said shoulder groove and said shaft groove of the nut member.

* * * * *